(12) United States Patent
McDevitt et al.

(10) Patent No.: US 9,510,816 B2
(45) Date of Patent: Dec. 6, 2016

(54) SELF-LOCKING SUTURE ANCHOR

(75) Inventors: Dennis McDevitt, Upton, MA (US); Jeffrey Halbrecht, San Francisco, CA (US); Richard Caspari, Maidens, VA (US)

(73) Assignee: DEPUY MITEK, LLC, Raynham, MA (US)

(*) Notice: Subject to any disclaimer, the term of this patent is extended or adjusted under 35 U.S.C. 154(b) by 2311 days.

(21) Appl. No.: 11/052,557

(22) Filed: Feb. 7, 2005

(65) Prior Publication Data

US 2005/0149122 A1 Jul. 7, 2005

Related U.S. Application Data

(63) Continuation of application No. 10/629,978, filed on Jul. 30, 2003, now Pat. No. 7,081,126, which is a continuation of application No. 10/375,389, filed on Feb. 27, 2003, now Pat. No. 6,660,023, which is a continuation of application No. 09/371,411, filed on Aug. 10, 1999, now Pat. No. 6,527,794.

(51) Int. Cl.
*A61B 17/04* (2006.01)
*A61F 2/08* (2006.01)
*A61B 17/00* (2006.01)

(52) U.S. Cl.
CPC ......... *A61B 17/0401* (2013.01); *A61F 2/0811* (2013.01); *A61B 90/03* (2016.02); *A61B 2017/00862* (2013.01); *A61B 2017/0403* (2013.01); *A61B 2017/044* (2013.01); *A61B 2017/045* (2013.01); *A61B 2017/0408* (2013.01); *A61B 2017/0412* (2013.01); *A61B 2017/0414* (2013.01); *A61B 2017/0424* (2013.01); *A61B 2017/0427* (2013.01); *A61B 2017/0438* (2013.01); *A61B 2017/0458* (2013.01); *A61B 2017/0459* (2013.01); *A61B 2090/037* (2016.02); *A61F 2002/0882* (2013.01)

(58) Field of Classification Search
CPC .............. A61B 2017/0403; A61B 2017/0408; A61B 2017/0422; A61B 2017/0424; A61B 2017/0425
USPC ................. 606/72, 139, 144, 148, 151, 232; 411/39–43
See application file for complete search history.

(56) References Cited

U.S. PATENT DOCUMENTS

| | | |
|---|---|---|
| 2,381,050 A | 12/1943 | Hardinge |
| 3,035,583 A | 5/1962 | Hirsch et al. |
| 3,036,482 A | 5/1962 | Kenworthy et al. |

(Continued)

FOREIGN PATENT DOCUMENTS

| | | |
|---|---|---|
| CA | 2153594 A1 | 7/1994 |
| CA | 2303853 A1 | 4/1999 |

(Continued)

OTHER PUBLICATIONS

EP Search Report for App No. 07253061.1 dated Mar. 10, 2008.

(Continued)

*Primary Examiner* — Tuan V Nguyen

(57) ABSTRACT

Methods, systems, and apparatuses are provided for attaching tissue, for example to bone. For example, devices are provided for anchoring filament to tissue or bone. Suture anchors are provided, and multi-component suture anchors are provided with sutures and components that fit together through an interference fit.

18 Claims, 4 Drawing Sheets

(56) References Cited

U.S. PATENT DOCUMENTS

| | | |
|---|---|---|
| 3,103,926 A | 9/1963 | Cochran et al. |
| 3,135,414 A | 6/1964 | Lee, II |
| 3,525,365 A | 8/1970 | Meulendyk et al. |
| 3,566,739 A | 3/1971 | Lebar |
| 3,708,883 A | 1/1973 | Flander |
| 3,760,802 A | 9/1973 | Fischer et al. |
| 3,842,824 A | 10/1974 | Neufeld |
| 4,013,071 A | 3/1977 | Rosenberg |
| 4,091,806 A | 5/1978 | Aginsky |
| 4,112,814 A | 9/1978 | Schafers |
| 4,140,111 A | 2/1979 | Morrill |
| 4,408,938 A | 10/1983 | Maguire |
| 4,447,915 A | 5/1984 | Weber |
| 4,475,856 A | 10/1984 | Toomingas |
| 4,484,570 A | 11/1984 | Sutter et al. |
| 4,492,226 A | 1/1985 | Belykh et al. |
| 4,498,468 A | 2/1985 | Hansson |
| 4,506,670 A | 3/1985 | Crossley |
| 4,590,928 A | 5/1986 | Hunt et al. |
| 4,632,100 A | 12/1986 | Somers et al. |
| 4,708,132 A | 11/1987 | Silvestrini |
| 4,711,232 A | 12/1987 | Fischer et al. |
| 4,716,893 A | 1/1988 | Fischer et al. |
| 4,738,255 A | 4/1988 | Goble et al. |
| 4,741,330 A | 5/1988 | Hayhurst |
| 4,760,843 A | 8/1988 | Fischer et al. |
| 4,778,468 A | 10/1988 | Hunt et al. |
| 4,790,304 A | 12/1988 | Rosenberg |
| 4,797,044 A | 1/1989 | Velasco |
| 4,834,752 A | 5/1989 | Van Kampen |
| 4,870,957 A | 10/1989 | Goble et al. |
| 4,871,289 A | 10/1989 | Choiniere |
| 4,873,976 A | 10/1989 | Schreiber |
| 4,924,865 A | 5/1990 | Bays et al. |
| 4,927,421 A | 5/1990 | Goble et al. |
| 4,940,467 A | 7/1990 | Tronzo |
| 4,944,742 A | 7/1990 | Clemow et al. |
| 4,988,351 A | 1/1991 | Paulos et al. |
| 5,013,316 A | 5/1991 | Goble et al. |
| 5,037,422 A | 8/1991 | Hayhurst et al. |
| 5,046,513 A | 9/1991 | Gatturna et al. |
| 5,059,206 A | 10/1991 | Winters |
| 5,078,718 A | 1/1992 | Moll et al. |
| 5,084,050 A | 1/1992 | Draenert |
| 5,116,337 A | 5/1992 | Johnson |
| 5,122,132 A | 6/1992 | Bremer |
| 5,141,373 A | 8/1992 | Kendall |
| 5,141,520 A | 8/1992 | Goble et al. |
| 5,152,735 A | 10/1992 | Podd, Jr. et al. |
| 5,152,763 A | 10/1992 | Johnson |
| 5,154,189 A | 10/1992 | Oberlander |
| 5,169,400 A | 12/1992 | Murling |
| 5,176,682 A | 1/1993 | Chow |
| 5,203,784 A | 4/1993 | Ross et al. |
| 5,207,579 A | 5/1993 | Campagnuolo |
| 5,207,679 A | 5/1993 | Li |
| 5,209,753 A | 5/1993 | Biedermann et al. |
| RE34,293 E | 6/1993 | Goble et al. |
| 5,224,946 A | 7/1993 | Hayhurst et al. |
| 5,236,445 A | 8/1993 | Hayhurst et al. |
| 5,244,946 A | 9/1993 | Guest et al. |
| 5,248,231 A | 9/1993 | Denham et al. |
| 5,257,637 A | 11/1993 | Gazayerli |
| 5,258,015 A | 11/1993 | Li et al. |
| 5,261,914 A | 11/1993 | Warren |
| 5,268,001 A | 12/1993 | Nicholson et al. |
| 5,269,783 A | 12/1993 | Sander |
| 5,314,427 A | 5/1994 | Goble et al. |
| 5,324,308 A | 6/1994 | Pierce |
| 5,326,205 A | 7/1994 | Anspach, Jr. et al. |
| 5,352,229 A | 10/1994 | Goble et al. |
| 5,354,298 A | 10/1994 | Lee et al. |
| 5,370,662 A | 12/1994 | Stone et al. |
| 5,380,334 A | 1/1995 | Torrie et al. |
| 5,400,805 A | 3/1995 | Warren |
| 5,411,523 A | 5/1995 | Goble |
| 5,417,712 A | 5/1995 | Whittaker et al. |
| 5,423,860 A | 6/1995 | Lizardi et al. |
| 5,441,502 A | 8/1995 | Bartlett |
| 5,458,601 A | 10/1995 | Young, Jr. et al. |
| 5,464,427 A * | 11/1995 | Curtis et al. ................. 606/232 |
| 5,466,243 A | 11/1995 | Schmieding et al. |
| 5,472,452 A | 12/1995 | Trott |
| 5,480,403 A | 1/1996 | Lee et al. |
| 5,486,197 A | 1/1996 | Le et al. |
| 5,489,210 A | 2/1996 | Hanosh |
| 5,496,326 A | 3/1996 | Johnson |
| 5,501,683 A | 3/1996 | Trott |
| 5,501,695 A | 3/1996 | Anspach et al. |
| 5,520,700 A | 5/1996 | Beyar et al. |
| 5,522,817 A | 6/1996 | Sander et al. |
| 5,522,844 A | 6/1996 | Johnson |
| 5,522,845 A | 6/1996 | Wenstrom, Jr. |
| 5,531,792 A | 7/1996 | Huene |
| 5,534,012 A | 7/1996 | Bonutti |
| 5,545,180 A | 8/1996 | Le et al. |
| 5,569,306 A | 10/1996 | Thal |
| 5,571,104 A | 11/1996 | Li |
| 5,584,835 A * | 12/1996 | Greenfield ................. 606/232 |
| 5,591,207 A * | 1/1997 | Coleman ..................... 606/232 |
| 5,601,558 A | 2/1997 | Torrie et al. |
| 5,626,614 A | 5/1997 | Hart |
| 5,643,320 A | 7/1997 | Lower et al. |
| 5,643,321 A * | 7/1997 | McDevitt ..................... 606/232 |
| 5,649,963 A | 7/1997 | McDevitt |
| 5,658,313 A | 8/1997 | Thal |
| 5,665,112 A | 9/1997 | Thal |
| 5,683,419 A | 11/1997 | Thal |
| 5,690,676 A | 11/1997 | DiPoto et al. |
| 5,702,397 A | 12/1997 | Goble et al. |
| 5,702,462 A | 12/1997 | Oberlander |
| 5,707,395 A | 1/1998 | Li |
| 5,709,708 A | 1/1998 | Thal |
| 5,713,903 A | 2/1998 | Sander et al. |
| 5,720,753 A | 2/1998 | Sander et al. |
| 5,720,765 A | 2/1998 | Thal |
| 5,725,529 A | 3/1998 | Nicholson et al. |
| 5,725,541 A | 3/1998 | Anspach, III et al. |
| 5,728,136 A | 3/1998 | Thal |
| 5,759,184 A | 6/1998 | Santangelo |
| 5,759,313 A | 6/1998 | Shirai et al. |
| 5,782,865 A | 7/1998 | Grotz |
| 5,791,899 A | 8/1998 | Sachdeva et al. |
| 5,797,963 A | 8/1998 | McDevitt |
| 5,800,436 A | 9/1998 | Lerch |
| 5,814,071 A | 9/1998 | McDevitt et al. |
| 5,814,072 A | 9/1998 | Bonutti |
| 5,814,073 A | 9/1998 | Bonutti |
| 5,845,645 A | 12/1998 | Bonutti |
| 5,849,004 A | 12/1998 | Bramlet |
| 5,860,978 A | 1/1999 | McDevitt et al. |
| 5,902,321 A | 5/1999 | Caspari et al. |
| 5,911,721 A | 6/1999 | Nicholson |
| 5,928,244 A | 7/1999 | Tovey et al. |
| RE36,289 E | 8/1999 | Le et al. |
| 5,935,129 A * | 8/1999 | McDevitt ........... A61B 17/0401 606/232 |
| 5,935,134 A | 8/1999 | Pedlick et al. |
| 5,948,000 A * | 9/1999 | Larsen et al. ................. 606/232 |
| 5,948,002 A | 9/1999 | Bonutti |
| 5,957,924 A | 9/1999 | Tormala et al. |
| 5,957,953 A | 9/1999 | DiPoto et al. |
| 5,968,044 A | 10/1999 | Nicholson et al. |
| 5,968,078 A | 10/1999 | Grotz |
| 5,980,558 A | 11/1999 | Wiley |
| 5,980,559 A | 11/1999 | Bonutti |
| 5,993,459 A | 11/1999 | Larsen et al. |
| 6,022,352 A | 2/2000 | Vandewalle |
| 6,039,740 A | 3/2000 | Olerud et al. |
| 6,042,584 A | 3/2000 | Pierson, III |
| 6,051,791 A | 4/2000 | King |
| 6,056,751 A | 5/2000 | Fenton, Jr. |
| 6,056,772 A | 5/2000 | Bonutti |
| 6,086,608 A * | 7/2000 | Ek et al. ..................... 606/232 |

(56) References Cited

U.S. PATENT DOCUMENTS

| | | | |
|---|---|---|---|
| 6,099,530 A | 8/2000 | Simonian et al. |
| 6,099,547 A | 8/2000 | Gellman et al. |
| 6,117,160 A | 9/2000 | Bonutti |
| 6,117,161 A | 9/2000 | Li et al. |
| 6,123,711 A | 9/2000 | Winters |
| 6,126,662 A | 10/2000 | Carmichael et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,669 A | 11/2000 | Li |
| 6,159,234 A | 12/2000 | Bonutti et al. |
| 6,162,234 A | 12/2000 | Freedland et al. |
| 6,162,236 A | 12/2000 | Osada |
| 6,165,203 A | 12/2000 | Krebs |
| 6,168,598 B1 | 1/2001 | Martello |
| 6,174,324 B1 | 1/2001 | Egan et al. |
| 6,200,329 B1 | 3/2001 | Fung et al. |
| 6,203,572 B1 | 3/2001 | Johnson et al. |
| 6,227,860 B1 | 5/2001 | Hobo |
| 6,228,096 B1 | 5/2001 | Marchand |
| 6,241,732 B1 | 6/2001 | Overaker et al. |
| 6,248,108 B1 | 6/2001 | Tormala et al. |
| 6,267,766 B1 | 7/2001 | Burkhart |
| 6,280,191 B1 | 8/2001 | Gordon |
| 6,290,701 B1 | 9/2001 | Enayati |
| 6,302,886 B1 | 10/2001 | McDevitt et al. |
| 6,309,405 B1 | 10/2001 | Bonutti |
| 6,319,252 B1 | 11/2001 | McDevitt et al. |
| 6,319,269 B1 | 11/2001 | Li |
| 6,332,778 B1 | 12/2001 | Choung |
| 6,368,326 B1 | 4/2002 | Dakin et al. |
| 6,391,030 B1 | 5/2002 | Wagner et al. |
| 6,413,260 B1 | 7/2002 | Berrevoets et al. |
| 6,423,062 B2 | 7/2002 | Enayati |
| 6,447,516 B1 | 9/2002 | Bonutti |
| 6,497,707 B1 | 12/2002 | Bowman et al. |
| 6,517,543 B1 | 2/2003 | Berrevoets et al. |
| 6,517,578 B2 | 2/2003 | Hein |
| 6,517,579 B1 | 2/2003 | Paulos et al. |
| 6,520,980 B1 | 2/2003 | Foerster |
| 6,524,316 B1 | 2/2003 | Nicholson et al. |
| 6,527,794 B1 | 3/2003 | McDevitt et al. |
| 6,547,792 B1 | 4/2003 | Tsuji et al. |
| 6,641,596 B1 | 11/2003 | Lizardi |
| 6,660,023 B2 | 12/2003 | McDevitt et al. |
| 6,673,094 B1 | 1/2004 | McDevitt et al. |
| 6,689,135 B2 | 2/2004 | Enayati |
| 6,689,140 B2 | 2/2004 | Cohen |
| 6,733,506 B1 | 5/2004 | McDevitt et al. |
| 6,770,073 B2 | 8/2004 | McDevitt et al. |
| 6,778,861 B1 | 8/2004 | Liebrecht et al. |
| 6,780,198 B1 | 8/2004 | Gregoire et al. |
| 6,840,953 B2 | 1/2005 | Martinek |
| 6,932,834 B2 | 8/2005 | Lizardi et al. |
| 7,074,203 B1 | 7/2006 | Johanson et al. |
| 7,081,126 B2 | 7/2006 | McDevitt et al. |
| 7,329,271 B2 | 2/2008 | Koyfman et al. |
| 7,357,810 B2 | 4/2008 | Koyfman et al. |
| 7,381,213 B2 | 6/2008 | Lizardi |
| 8,491,600 B2 | 7/2013 | McDevitt et al. |
| 8,518,091 B2 | 8/2013 | McDevitt et al. |
| 2001/0005475 A1 | 6/2001 | Frigg |
| 2001/0053913 A1 | 12/2001 | Freedland |
| 2002/0040241 A1 | 4/2002 | Jarvinen |
| 2002/0115999 A1 | 8/2002 | McDevitt et al. |
| 2002/0147463 A1 | 10/2002 | Martinek |
| 2003/0004545 A1 | 1/2003 | Burkhart et al. |
| 2003/0130695 A1 | 7/2003 | McDevitt et al. |
| 2003/0167062 A1 | 9/2003 | Gambale et al. |
| 2003/0187446 A1 | 10/2003 | Overaker et al. |
| 2003/0204193 A1 | 10/2003 | Gabriel et al. |
| 2004/0181234 A1 | 9/2004 | McDevitt et al. |
| 2004/0220573 A1 | 11/2004 | McDevitt et al. |
| 2005/0033364 A1 | 2/2005 | Gregoire et al. |
| 2005/0055052 A1 | 3/2005 | Lombardo et al. |
| 2005/0090862 A1 | 4/2005 | McDevitt et al. |
| 2005/0149122 A1 | 7/2005 | McDevitt et al. |
| 2005/0216059 A1 | 9/2005 | Bonutti et al. |
| 2006/0079904 A1 | 4/2006 | Thal |
| 2006/0161159 A1 | 7/2006 | Dreyfuss et al. |
| 2006/0235413 A1 | 10/2006 | Denham et al. |
| 2006/0264951 A1 | 11/2006 | Nelson et al. |
| 2006/0282081 A1 | 12/2006 | Fanton et al. |
| 2007/0038230 A1 | 2/2007 | Stone et al. |
| 2007/0142846 A1 | 6/2007 | Catanese et al. |
| 2007/0219557 A1 | 9/2007 | Bourque et al. |
| 2008/0033460 A1 | 2/2008 | Ziniti et al. |
| 2008/0033486 A1 | 2/2008 | Whittaker et al. |
| 2009/0099598 A1 | 4/2009 | McDevitt et al. |
| 2009/0248068 A1 | 10/2009 | Lombardo et al. |
| 2009/0318964 A1 | 12/2009 | Lombardo et al. |
| 2009/0326579 A1 | 12/2009 | Anderhub et al. |
| 2011/0098728 A1 | 4/2011 | McDevitt |
| 2011/0152885 A1 | 6/2011 | McDevitt |
| 2011/0152929 A1 | 6/2011 | McDevitt et al. |

FOREIGN PATENT DOCUMENTS

| | | |
|---|---|---|
| DE | 3406961 | 9/1985 |
| DE | 8520206 U1 | 12/1985 |
| EP | 58744 | 5/1984 |
| EP | 241240 | 10/1987 |
| EP | 124489 | 1/1988 |
| EP | 251583 | 1/1988 |
| EP | 260970 | 3/1988 |
| EP | 270704 | 4/1989 |
| EP | 232049 | 3/1990 |
| EP | 0390613 A1 | 10/1990 |
| EP | 340159 | 1/1993 |
| EP | 0589306 | 3/1994 |
| EP | 409364 | 9/1994 |
| EP | 574707 | 8/1997 |
| EP | 611557 | 4/1999 |
| EP | 1206924 A1 | 5/2002 |
| EP | 1844715 A2 | 10/2007 |
| EP | 2084468 A2 | 8/2009 |
| FR | 2054731 | 5/1971 |
| FR | 2346591 | 10/1977 |
| FR | 2622430 | 5/1989 |
| FR | 2682867 A1 | 4/1993 |
| GB | 2084468 | 4/1982 |
| GB | 2248778 | 4/1992 |
| JP | 5512951 | 9/1975 |
| JP | 6505888 T | 7/1994 |
| JP | 11-503931 A | 4/1999 |
| JP | 2000120628 A | 4/2000 |
| JP | 2001-501112 A | 1/2001 |
| JP | 2001-161883 A | 6/2001 |
| JP | 2002-177286 A | 6/2002 |
| JP | 2002-282258 A | 10/2002 |
| JP | 2004-160177 A | 6/2004 |
| JP | 2005-110984 A | 4/2005 |
| JP | 2005-511189 A | 4/2005 |
| JP | 2005-523103 A | 8/2005 |
| WO | WO 8809157 | 12/1988 |
| WO | WO 8901767 | 3/1989 |
| WO | WO 9204874 | 4/1992 |
| WO | WO 9502998 | 2/1995 |
| WO | WO 9515726 | 6/1995 |
| WO | WO 9529636 | 11/1995 |
| WO | 9602193 | 2/1996 |
| WO | 9729693 | 8/1997 |
| WO | WO 9838938 | 11/1998 |
| WO | 9922648 A1 | 5/1999 |
| WO | 0106909 A2 | 2/2001 |
| WO | 03049620 A1 | 6/2003 |

(56) References Cited

FOREIGN PATENT DOCUMENTS

| | | |
|---|---|---|
| WO | 2005/102190 A3 | 5/2006 |
| WO | 2006128092 A2 | 11/2006 |

OTHER PUBLICATIONS

EP Search Report for App No. 07253063.7 dated Nov. 29, 2007.
Japanese Official Action for JP Application No. 2001-351434, prepared Oct. 10, 2007. (2 pages).
Supplementary Partial EP Search Report for App. No. 00950502.5 dated May 16, 2008.
Japanese Office Action for Application No. 2007-203527, issued Jun. 5, 2012 (English translation).
Japanese Office Action for Application No. 2007-203520, issued Jun. 5, 2012 (English translation).

* cited by examiner

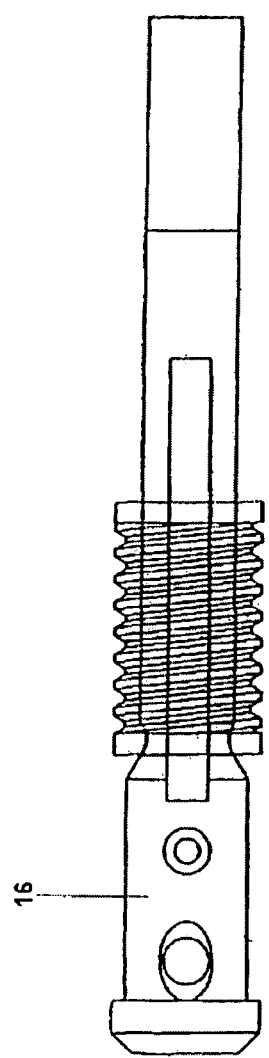
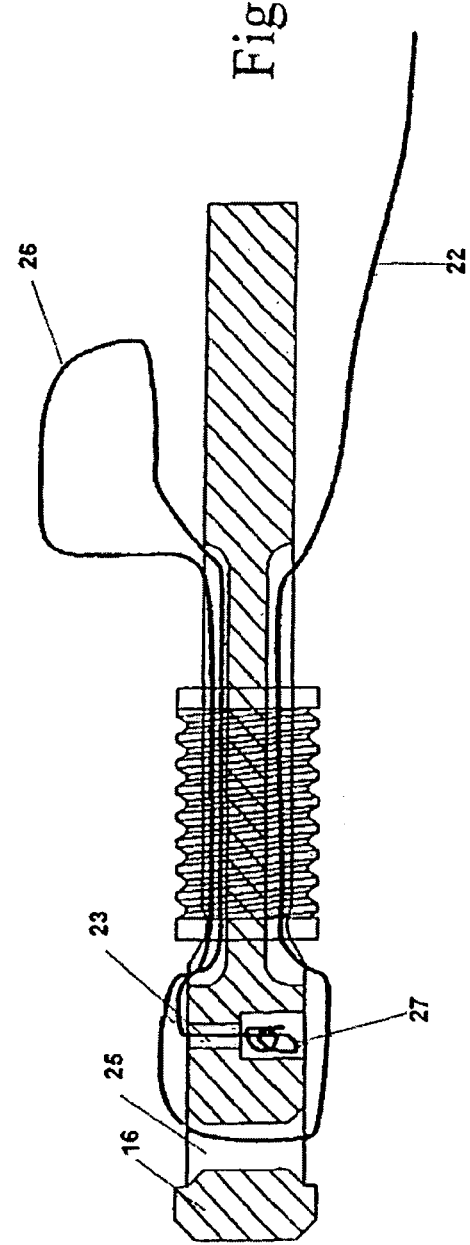

SELF-LOCKING SUTURE ANCHOR

CROSS-REFERENCE TO RELATED APPLICATIONS

This application is a continuation of U.S. patent application Ser. No. 10/629,978 filed on Jul. 30, 2003 and entitled "Self-Locking Suture Anchor,"now U.S. Pat. No. 7,081,126, which is a continuation of U.S. Pat. No. 6,660,023 filed on Feb. 27, 2003 and entitled "Self-Locking Suture Anchor," which is a continuation of U.S. Pat. No. 6,527,794 filed on Aug. 10, 1999 and entitled "Self-Locking Suture Anchor." These references are hereby incorporated by reference in their entirety.

BACKGROUND OF THE INVENTION

This invention relates to surgical fasteners, e.g., anchors that secure sutures to bone, a meniscus, or other tissue. It further relates to a suture anchor that attaches a suture to tissue without the use of knots, and to methods of securing tissue using one or more anchors and a length of suture.

Many surgical procedures require the attachment of soft tissue, e.g., ligament or tendon grafts, to bone. This is typically accomplished by anchoring a suture in bone, for example with a screw, pin, or other bone anchoring device, and looping the suture around or stitching the suture to the soft tissue. When this process is completed, the surgeon generally must knot the suture to secure the tissue. This knotting process can be difficult and tedious, particularly during laparoscopic or endoscopic procedures, where the surgeon must remotely manipulate the suture using tools inserted through an endoscopic tube. Further, as many as six knots are often required to secure one suture. These knots may "stand proud" above the tissue and interfere with movement and healing.

One advance which has been proposed is the anchor apparatus disclosed by Goble, et al., in U.S. Pat. No. 5,702,397. That apparatus comprises an anchor body through which a suture passes, and which contains a clamping mechanism such as a spherical element within the anchor body. When the suture is pulled in a proximal direction, the clamp is urged into contact with the anchor body, thereby holding the suture in place. When the suture is pulled in a distal direction, the clamp disengages, and the suture can move freely through the anchor body. At least one end of the suture is stitched and/or knotted to soft tissue.

Several knotless suture anchor assemblies have recently been proposed by Thal in U.S. Pat. Nos. 5,569,306; 5,658,313; 5,665,112; and 5,683,419. These describe suture anchors which secure a filament having a small loop at one end. In some embodiments, another length of suture ends in a small block, which is passed through the loop to secure the tissue. While these structures can be secured without knots, the block used to secure the suture may itself stand proud above the tissue, causing discomfort and interfering with healing. In other embodiments, the anchor itself is passed through the small loop, creating a larger loop which is used to hold tissue.

U.S. Pat. No. 5,709,708, also by Thal, describes a suture anchor utilizing a continuous loop of suture material, which secures the tissue in a similar manner. As in the other Thal knotless anchors, the tension of the suture is dependent on the length of specially provided suture, which cannot be adjusted. Thus, these anchors cannot be used in surgical operations in which it is necessary to tighten a loop of suture to secure soft tissue.

The tying of suture knots presents difficulties in other surgical procedures, as well. For example, tears occur commonly in the menisci of athletes. The simplest method of repairing such a tear is to stitch it closed by passing a length of suture through the tissue and tying. However, the needles used in such surgery are very difficult to manipulate during endoscopic surgery, and the knots used to secure the suture may interfere with healing as described above. These difficulties are particularly severe in the restricted space of the joint capsule of the knee, a common location for such injuries. Other devices such as darts and clamps have also been proposed for this purpose; see for example U.S. Pat. Nos. 5,154,189; 5,269,783; and 5,702,462. Like suture knots, these devices may cause considerable discomfort during healing of the tear. Further, if made of non-bioabsorbable materials, a second surgery must be performed to remove the devices from the meniscus after healing.

A need thus exists for an improved technique and apparatus for securing tissues without the use of knots. A further need exists for such techniques and apparatus which also permit the position of the suture to be readily adjusted. A still further need exists for such apparatus which is small enough to avoid discomfort, which is amenable to fabrication from bioabsorbable materials, and which can be used either in bone or in soft tissue.

SUMMARY OF THE INVENTION

The above needs are among those met by the invention, which provides an anchoring device that can be embedded in bone or soft tissue, that permits suture length and/or tension to be readily adjusted, and that can be secured without the use of knots.

In one aspect of the invention, a suture anchor suitable to be embedded in bone has a cavity which holds a filament (e.g., a suture) by interference fit. The anchor holds the suture tightly enough to resist "operational" forces to which the suture is subjected subsequent to deployment, e.g., during movement of the bones and/or soft tissues to which the suture is attached. However, the interference fit is weak enough to allow the suture to be pulled longitudinally through the cavity by a stronger force.

In use, such an anchor can be placed with some slack in the suture. The suture can then be tightened by pulling on one of its ends (with the larger force). It is an advantage of the invention that the tightening of the suture can be reversed, simply by pulling on a loop formed by the suture or by pulling on its opposite end. The suture does not loosen in normal use, however, since the forces required to move during deployment are greater than those exerted by the bones and/or tissues to which it is attached.

In a related aspect, the anchor may hold the suture at two points, forming a loop. The loop can be disposed around tissue and, then, tightened by pulling one end of the suture, thereby securing the tissue. Again, if the loop is drawn too tight, it can be loosened by pulling firmly.

The invention also provides methods for attaching soft tissue to bone. In these methods, an anchor of the type described above can be emplaced in bone. The soft tissue is secured by stitching or by catching a portion of the tissue in a loop of suture, which is subsequently tightened. The suture can be tightened or loosened as necessary during deployment, and need not be knotted.

These and other aspects of the invention are evident in the drawings and in the description that follows.

BRIEF DESCRIPTION OF THE DRAWINGS

The invention is best understood with reference to the drawings, in which:

FIG. 3 is an illustration of a suture anchor according to the invention before deployment.

DETAILED DESCRIPTION OF PREFERRED EMBODIMENTS

Figure 1A:
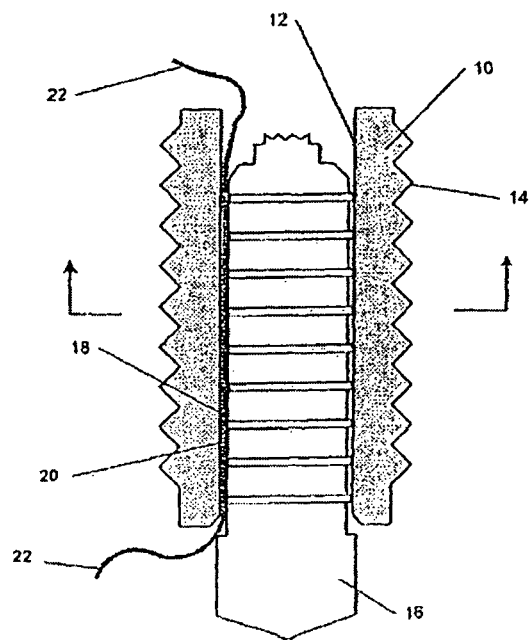
FIGS. 1 and 2 are illustrations of suture anchors according to the invention, adapted to be embedded in bone.

FIG. 1*a* shows a cutaway view of a suture anchor according to the invention. The anchor comprises an anchoring element 10, which is adapted to be embedded in a bone tunnel or in soft tissue, and comprises an axial channel 12. In the embodiment shown, element 10 comprises a series of ridges 14 on its outer surface, which aid in securing the element, for example, in a bone tunnel. It will be understood that the ridges 14 are not a necessary element of the anchor, and may be omitted if desired. The anchor 10 further comprises an insertion stem 16. When the anchor is in the deployed position shown in FIG. 1*a*, the insertion stem 16 is held within the axial channel 12, e.g., by interference fit. In preferred embodiments, the insertion stem 16 is slightly larger than the axial channel 12, so that the stem 16 forces the anchoring element 10 to expand when it is inserted therein, thereby securing the anchor firmly in the bone tunnel.

Figure 1B:
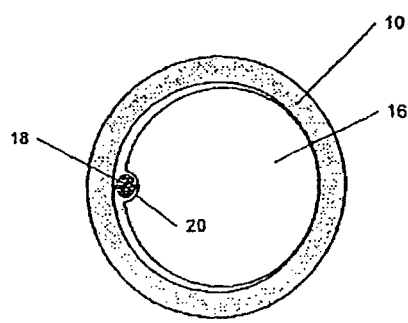

The anchor further comprises a filament 18, e.g., a suture, disposed between the anchoring element 10 and the insertion stem 16. In the preferred embodiment shown in FIGS. 1*a* and 1*b*, the insertion element comprises a suture channel 20. This channel guides the suture 18, and holds it in compression against the anchoring element 10. The configuration of anchoring element 10, insertion stem 16, and suture 18 can be seen clearly in FIG. 1*b*, which shows a cross-sectional view of the anchor at the point indicated by the arrows of FIG. 1*a*. The mild compression of the suture 18 in the channel 20 provides a frictional resistance to prevent movement of the suture when tension is applied to one of its free ends 22. This frictional resistance is overcome when a tension greater than the threshold tension is applied to a free end of the suture. The suture 18 may then slide longitudinally through the channel 20, allowing the length of the free ends 22 to be adjusted.

It will be understood that the configuration of suture 18 in FIG. 1 represents only one of many possible embodiments of the invention. In particular, it will often be preferable to pass the suture between the insertion stem 16 and the anchoring element 10 multiple times, for example, in order to form a loop segment. In other embodiments of the invention, the compression of the suture may be stronger, so that the threshold tension which would be necessary to move the suture is close to or exceeds the breaking strength of the suture. In such embodiments, the length of the free ends is no longer adjustable once the compression on the suture is applied.

Figure 2A:
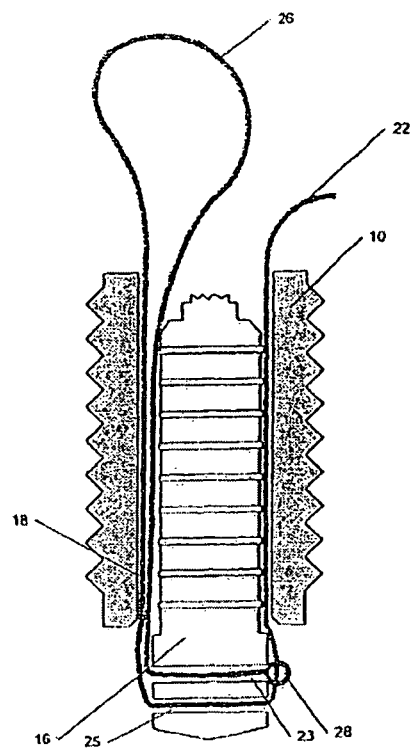
Figure 2B:
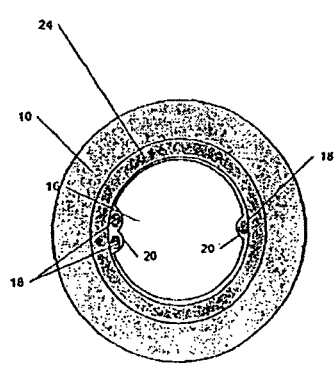

In one such embodiment, the suture (or other filament) may be formed with a small loop at one end, which is used to secure the suture to the anchor. This embodiment is illustrated in FIGS. 2*a* and 2*b*; the former depicting a cross-section of the anchor along the axis of symmetry; and the latter depicting a transverse section. The head of suture 18 comprises a small loop 28; e.g., disposed at the distal end of the anchor. The suture passes between the insertion stem 16 and the anchoring element 10, forms a loop segment 26, and passes back between the insertion stem and the anchoring element. The suture then passes through head loop 28, back up between the insertion stem 16 and the anchoring element 10, and ends in free end 22. The loop segment 26 can be tightened by pulling free end 22, and loosened by pulling the loop segment 26 itself. Because of the mechanical advantage afforded by looping of the suture, the force required to loosen the suture by pulling on loop 26 is twice the force required to tighten the suture by pulling on free end 22. In the embodiment shown, the suture passes through two channels 23, 25 in the anchor 16; one of these channels 25 could be eliminated so that the suture would pass around the head of the anchor.

FIGS. 3*a* and 3*b* illustrate a different embodiment of the anchor, in which the suture is secured by a small knot 27 rather than a loop. FIG. 3*a* is a plan view of the anchor, and FIG. 3*b* is a longitudinal cross-section.

Figure 4A:
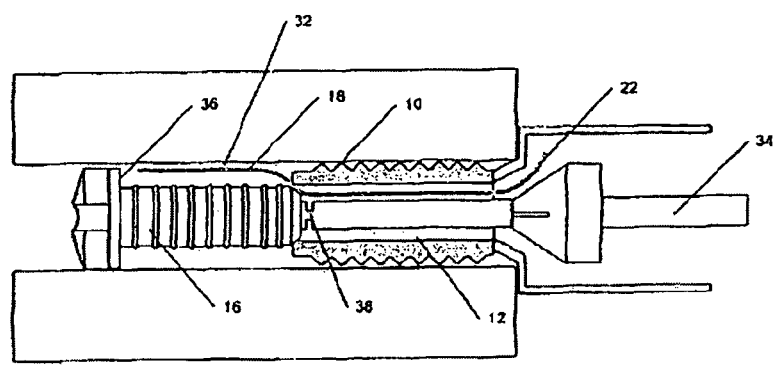
FIGS. 4A-4C illustrate a deployment process for the anchors shown in FIGS. 1 and 2.
Figure 4B:
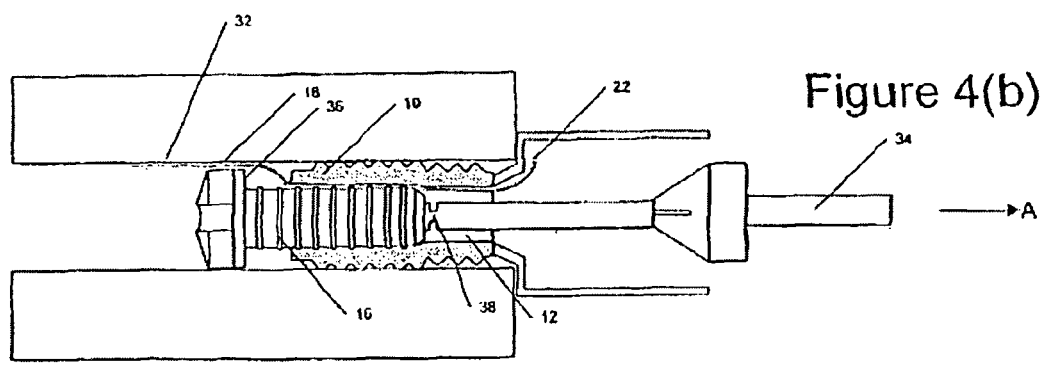
Figure 4C:
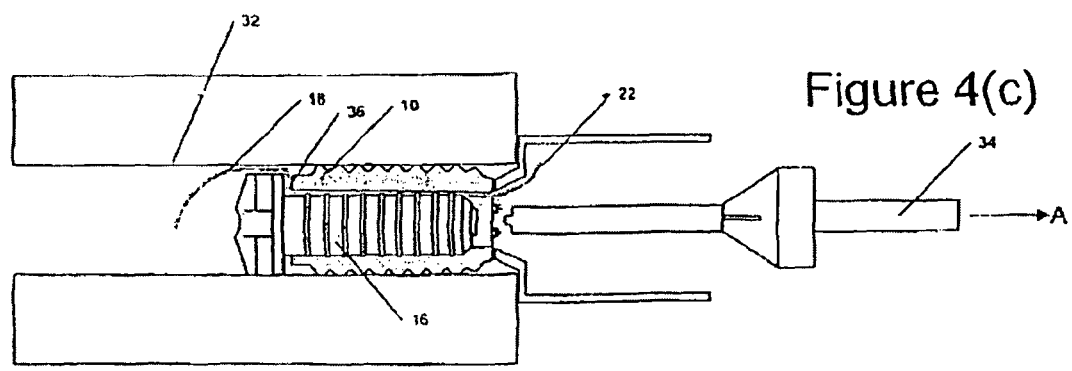

FIGS. 4*a*-4*c* illustrate a deployment process for the anchors shown in FIGS. 1 and 2. Only a portion of the suture is shown in FIGS. 4*a*-4*c*; preferably, the suture will be looped in the fashion shown in FIG. 2 or FIG. 3. FIG. 4*a* shows an anchor placed in bone tunnel 32, connected to deployment apparatus 34. FIG. 4*b* illustrates the insertion element 16 being pulled into the axial channel 12 of anchoring element 10. Tension is applied to the stem of insertion element 16 (in the direction shown by arrow A) by the colleted stem-pulling portion of the deployment device 34, while the anchoring element 10 is held substantially immobile within bone hole by the anchor-holding portion of that device. These forces act to move the insertion element 16 in the direction of arrow A such that larger diametered portion of insertion element is pulled into the axial channel 12 of anchoring element 10. As a result, the wall of the anchoring element 10 expands outwardly and into the walls of the bone hole 32. As shown in FIG. 4*c*, the insertion stem is pulled proximally through the axial bore 12, until further motion is retained by abutment of flange 36 with the distal end of anchoring element 10. At this point, the deployment device continues to exert tension on the stem 16, causing frangible portion 38 to shear. This facilitates removal of the excess portion of the stem 16 and, likewise, disengages the deployment device 34. The suture 18 can be adjusted by pulling firmly on free end 22.

The suture anchors of the invention can be provided in a variety of sizes and materials, depending on the intended application. For example, a typical anchor intended to be embedded in the shoulder blade, for use in repair of the rotator cuff of an adult, might have a length in the range of 8-15 mm and a diameter in the range of 3-6 mm. Such an anchor might be capable, for example, of holding a #2 suture with a threshold force in the range of 25-35 lbs. (As it is used herein, the term "threshold force" describes a pulling force above which a filament moves longitudinally through an anchor, and below which the filament substantially does not move through the anchor). It is generally desirable for the anchor to consist of biocompatible material, e.g., implant grade high density polyethylene, low density polyethylene (PE 6010 and PE 2030), polypropylene (13R9A and 23M2: all made by Rexene, Dallas, Tex.) or surgical implant grade steel. In some embodiments, the anchor may comprise a bioabsorbable material, e.g., poly-1-lactide or a lactide-glycolide composition.

In an exemplary embodiment of the methods of the invention, the anchor illustrated in FIGS. 3*a* and 3*b* can be used to repair a torn rotator cuff by reattachment of the rotator cuff to the scapula. An anchor such as that illustrated in FIG. 3*a*, which holds a loop of suture by interference fit, is embedded in a tunnel drilled, for example, in the scapula. The loop of suture and the free end of the suture extend out from the scapula at the proximal end of the anchor.

When the anchor is disposed in the bone tunnel, a portion of the torn rotator cuff is passed through the suture loop. The loop is then tightened by pulling with a force greater than the threshold force on the free end of the suture. This tightens the loop, drawing the tissue against the anchor and securing it to the bone without knotting the suture. The free end of the suture may then be trimmed, if desired.

The invention may be used with various anchor designs, depending on the nature of the surgical repair. In particular, designs similar to those described in U.S. application Ser. No. 08/813,914, now U.S. Pat. No. 5,935,129, e.g., at FIG. 5 and in the accompanying text, and in U.S. application Ser. No. 08/814,149, now U.S. Pat. No. 5,911,721, and in the accompanying text, both of which are incorporated herein by reference, may be adapted to hold a suture in accordance with the teachings herein.

Other embodiments of the invention will be apparent to those skilled in the art from a consideration of the specification or practice of the invention disclosed herein. For example, while the invention has been described primarily in the contexts of securing soft tissue to bone and of repairing tears in soft tissue, it may also be used to secure or repair cartilage, ligaments, or other tissues. It is intended that the specification and examples be considered as exemplary only, with the true scope and spirit of the invention being indicated by the following claims.

What is claimed is:

1. A device for anchoring a filament to tissue or bone, comprising:
    a first component adapted to be embedded in bone and having a cavity formed therein;
    a second component configured to be pulled proximally into a distal end of the first component to expand the first component in a distal-to-proximal direction, and such that the first and second components are effective to retain a filament therebetween, the second component being retained within the first component by an interference fit formed between the first and second components, and the second component including a frangible portion at a proximal end that is adapted to shear after the second component is pulled into the first component; and
    a filament having first and second ends, the filament extending between the first component and the second component and having a closed end of a loop positioned proximal of a proximal end of the first component and having only the first end of the filament extending from the proximal end of the first component.

2. The device of claim 1, wherein the second component includes a flange formed on a terminal end thereof, the flange having an outer diameter that is greater than an inner diameter of the cavity in the first component to prevent insertion of the flange into the cavity.

3. The device of claim 2, wherein the flange is formed on a distal end of the second component, and the frangible portion is formed on a proximal end of the second component.

4. The device of claim 1, further comprising an elongate deployment member attached to the second component by the frangible portion, wherein the frangible portion is adapted to shear upon application of a force applied to the elongate deployment member.

5. The device of claim 1, wherein the filament extends through the cavity in the first component.

6. A device for anchoring a filament to tissue or bone, comprising:
    an anchor having first and second components adapted to retain a suture therebetween, the second component being receivable within the first component and held therein by an interference fit formed between the first and second components;
    an elongate shaft frangibly attached to a proximal end of the second component and configured to pull the second component into the first component to expand the first component in a distal-to-proximal direction; and
    a suture extending between the anchor and the elongate shaft and having a closed end of a loop segment extending from a proximal end of the first component and having only one free end extending from the proximal end of the first component.

7. The device of claim 6, wherein the second component includes a flange formed on a terminal end thereof and adapted to abut a terminal end of the first component.

8. The device of claim 7, wherein the flange is formed on a distal end of the second component, and a proximal end of the second component is frangibly attached to the elongate shaft.

9. The device of claim 6, wherein the elongate shaft is frangibly attached to the second component by a frangible portion that is adapted to shear upon application of a force applied to the elongate shaft.

10. The device of claim 6, wherein the elongate shaft is frangibly coupled to a proximal end of the second component and a distal end of the second component includes a flange defining a maximum outer diameter of the second component.

11. A suture anchor, comprising:
    an elongate anchor element adapted to be embedded in bone and having a cavity formed therein with opposite open ends;
    an elongate insertion element adapted to be received within the cavity in the elongate anchor element to expand the elongate anchor element in a distal-to-proximal direction such that the elongate insertion element is held within the elongate anchor element by an interference fit formed between the elongate anchor element and the elongate insertion element;
    a suture having a first end and a second end, the suture extending through at least a portion of the cavity and positioned between the elongate anchor element and the elongate insertion element, wherein the suture includes a closed end of a loop segment positioned proximal of a proximal end of the elongate anchor element and the first end of the suture extends from the proximal end of the elongate anchor element; and
    an elongate shaft frangibly attached to a proximal end of the elongate insertion element and configured to pull the elongate insertion element into the elongate anchor element.

12. The suture anchor of claim 11, wherein the elongate insertion element includes a proximal end frangibly attached to the elongate shaft and a distal end having a flange that abuts a distal end of the elongate anchor element.

13. A suture anchor, comprising:
    an elongate anchor element adapted to be embedded in bone and having a cavity formed therein with opposite open ends:
    an elongate insertion element adapted to be received within the cavity in the elongate anchor element to expand the elongate anchor element in a distal-to-proximal direction such that the elongate insertion element is held within the elongate anchor element by an interference fit formed between the elongate anchor element and the elongate insertion element;
    a suture extending through at least a portion of the cavity and positioned between the elongate anchor element and the elongate insertion element, wherein the suture extends between the elongate anchor element and the elongate insertion element and includes a loop segment extending from a proximal end of the elongate anchor element; and an elongate shaft frangibly attached to a proximal end of the elongate insertion element and configured to pull the elongate insertion element into the elongate element, wherein the insertion element and the elongate anchor element are adapted to hold the suture therebetween by a compression fit.

14. A suture anchor, comprising:

an anchor element adapted to be embedded in bone and having a cavity formed therein;

an insertion element adapted to be received within the cavity in the anchor element to expand the anchor element in a distal-to-proximal direction such that the insertion element is held within the anchor element by an interference fit formed between the anchor element and the insertion element, the insertion element including a flange formed on a distal end thereof and adapted to abut a distal end of the anchor element;

an elongate shaft frangibly attached to a proximal end of the insertion element for inserting the insertion element into the anchor element; and a suture having first and second ends, the suture extending between the anchor element and the insertion element and having a closed end of a loop segment extending from a proximal end of the anchor element and having only one of the first and second ends of the suture extending from the proximal end of the anchor element.

15. The suture anchor of claim 14, wherein the cavity includes opposite open ends.

16. The suture anchor of claim 14, wherein the anchor element and the insertion element are adapted to retain the suture therebetween.

17. The suture anchor of claim 14, wherein the elongate shaft is frangibly attached to a proximal end of the insertion element and the flange is formed on a distal end of the insertion element.

18. A suture anchor, comprising:

an elongate anchor element adapted to be embedded in bone and having a cavity formed therein;

an insertion element adapted to be received within the cavity in the anchor element to expand the anchor element in a distal-to-proximal direction such that the insertion element is held within the anchor element by an interference fit formed between the anchor element and the insertion element, the insertion element including a flange formed on a distal end thereof and adapted to abut a distal end of the anchor element;

an elongate shaft frangibly attached to a proximal end of the insertion element for inserting the insertion element into the anchor element; and a suture extending between the anchor element and the insertion element and having a loop segment extending from a proximal end of the anchor element, wherein the anchor element and the insertion element are adapted to retain the suture therebetween by compression fit.

\* \* \* \* \*